United States Patent [19]

Eller et al.

[11] Patent Number: 4,695,647

[45] Date of Patent: Sep. 22, 1987

[54] AROMATIC DERIVATIVES OF 13-AZAPROSTANOIC ACID

[75] Inventors: Thomas D. Eller, Mt. Pleasant; Perry V. Halushka; Daniel R. Knapp, both of Charleston; Dale Mais, Goose Creek, all of S.C.

[73] Assignee: Drug Science Foundation, Charleston, S.C.

[21] Appl. No.: 592,074

[22] Filed: Mar. 22, 1984

[51] Int. Cl.$^4$ .......................................... C07C 177/00
[52] U.S. Cl. ..................................................... 560/53
[58] Field of Search ......................................... 560/53

[56] References Cited

U.S. PATENT DOCUMENTS

4,166,187 8/1979 Bundy ................................... 560/55
4,239,778 12/1980 Venton et al. ...................... 424/305

FOREIGN PATENT DOCUMENTS

44711 1/1982 European Pat. Off. .
2548955 5/1970 Fed. Rep. of Germany .
2814711 10/1978 Fed. Rep. of Germany .
60-4154 1/1985 Japan .

OTHER PUBLICATIONS

Venton et al, "Azaprostanoic Acid Derivatives, Inhibitors of Arachidonic Acid Induced Platelet Aggregation", *Journal of Medicinal Chemistry*, 1979, vol. 22, No. 7, pp. 824–830.
R. J. K. Taylor, pp. 159–190, "Synthesis of Analogues of Prostaglandin Endoperoxides".
Liebigs Ann. Chem., 1982, 150–166, H. Disselnkotter, F. Lieb, H. Oediger und D. Wendisch, "Synthese von Prostaglindin-Analoga".
Tetrahedron Letters, vol. 25, No. 38, pp. 420–4210, 1984-Great Britain, "Synthesis of Thromboxane Receptor Antagonists with the Potential to Radiolabel with I$^{125}$.
"Specific Binding of [125-I]-p-OH-SQ 28,668 in Human Platelet Membranes by Anders Hedberg, Edward C.-K. Liu, Steven E. Hall, Jan. I. Tu and Sidney A. Gilman-Poster Pager presented at ASPET (B), Spring, 1985.
The Journal of Clinical Investigation, vol. 56, Dec. 1975, 1404–1410—"Metabolism of Prostaglandins A$_1$ and E$_1$ in Man", Michael Golub, Priscilla Zia, Masayoshi Matsuno and Richard Horton.
Biochimica et Biophysica Acta, 431 (1976), 139–146, $^{125}$I Derivatives of Prostaglandins—A Novel Approach in Prostaglandin Analysis by Radioimmunoassay—Jacques Maclouf, Michelle Pradel, Philippe Pradelles and Fernand Dray.
The Journal of Pharmacology and Experimental Therapeutics, vol. 233, No. 2, pp. 418–424 by D. E. Mais, D. L. Saussy, Jr., A. Chaikhouni, P. J. Kochel, D. R. Knapp, N. Hamanaka and P. V. Halushka.

*Primary Examiner*—Paul J. Killos
*Attorney, Agent, or Firm*—Pahl, Lorusso & Loud

[57] ABSTRACT

Novel substituted phenyl eicosanoid analogs having the formula:

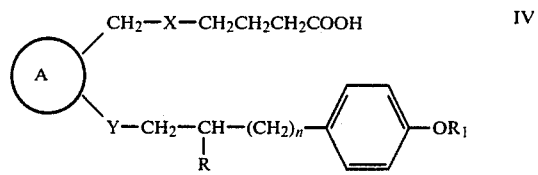

and their pharmaceutically acceptable esters and salts, wherein:
R is H or OH;
R$_1$ is H or lower alkyl;
X is —CH$_2$—CH$_2$— or cis —CH=CH—;
Y is —CH$_2$—,

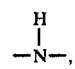

—O— or —S—;
n is 0 or 1; and
Ⓐ is (1) an eicosanoid nucleus (ring system), (2) a carbocyclic analog of an eicosanoid nucleus or (3) a heterocyclic analog of an eicosanoid nucleus wherein one of the carbons in a carbocyclic analog is replaced by O, S or N.

11 Claims, No Drawings

AROMATIC DERIVATIVES OF 13-AZAPROSTANOIC ACID

The invention described here was in the course of work under Grant No. GM20387 and Grant No. HL-29556 from the Department of Health and Human Services.

BACKGROUND OF THE INVENTION

Thrombotic conditions such as myocardial infarction, stroke and pulmonary embolism all occur through formation, by platelet aggregation, of a platelet plug or thrombus. Knowledge gained in recent years with regard to the mechanism of platelet aggregation has led to the development of new drugs designed to treat thrombotic conditions by control of the platelet aggregation mechanism. More specifically, it is now known that the aggregation of human platelets in plasma occurs in two phases. The first phase is initiated by the presence of adenosine diphosphate (ADP) and is characterized by the clumping of platelets. The second phase, in which the platelets are irreversibly bound, is induced by the presence of arachidonic acid which is metabolized within the platelet to form Thromboxane $A_2$ ($TXA_2$) through certain endoperoxide intermediates in what has been termed the arachidonic acid cascade. $TXA_2$ or certain endoperoxide intermediates, in turn, are believed to operate upon a receptor to effect platelet aggregation. Most work to date in this area has focused on reducing in vivo platelet reactivity (in the second phase) by specific inhibition of $TXA_2$ synthesis or by blocking of the $TXA_2$/endoperoxide receptor.

The compound (I), 13-Azaprostanoic acid, is a known thromboxane $A_2$ receptor antagonist and may be represented by the following formula:

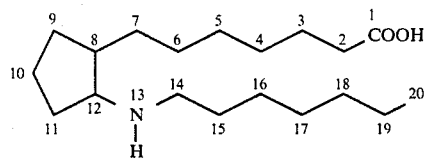

Venton, Le Breton and Enke in U.S. Pat. No. 4,239,778 and in "Azaprostanoic Acid Derivatives. Inhibitors of Arachidonic Acid Induced Platelet Aggretation", *J. Med. Chem.* 1979, Vol. 22, No. 7, pp. 824-830 teach that certain azaprostanoic acid derivatives are potent inhibitors of platelet aggregation. In their literature article, Venton et al describe the only aryl compound which they tested, a 14-benzyl derivative, as being totally inactive.

In order to further elucidate the platelet aggregation process, various studies of the binding of thromboxane receptors have been conducted using tritium labelled 13-APA. However, the extent of these studies has been limited by the relatively low level of radioactivity of tritium and the weak potency of 13-APA. Accordingly, a need has existed for a more potent thromboxane receptor blocker which can be labelled with a more highly radioactive substance.

SUMMARY OF THE INVENTION

It has now been discovered that certain substituted phenyl analogs of the naturally occuring eicosanoids are potent antagonists of platelet aggregation and vasoconstrictors and that other analogs are agonists of platelet aggregation. The naturally occuring eicosanoids are twenty carbon carboxylic acids produced within the human body as metabolites of arachidonic acid in the aforementioned arachidonic acid casade. With one known exception, all naturally occurring eicosanoids can be represented by the following formula:

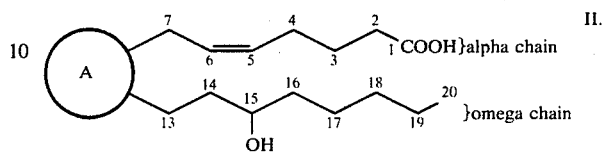

wherein Ⓐ is a five carbon carbocyclic or heterocyclic nucleus or ring system. In the known cicosanoid heterocyclic ring systems, oxygen is the hetero atom, e.g., Thromboxane A and B and the endoperoxides. Thus, with the one noted exception, all eicosanoids are characterized by a five carbon ring, a seven carbon, carboxyl terminated alpha side chain having a double bond and an eight carbon omega side chain also having a double bond. The single known exception is prostaglandin I (PGI) which has the formula:

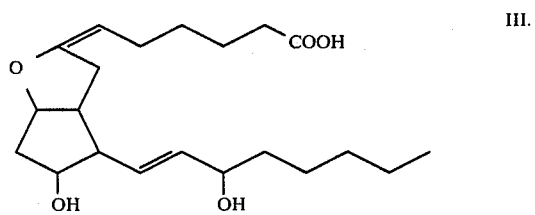

The ring systems Ⓐ in formula II are as follows:

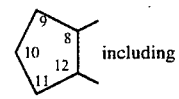 including

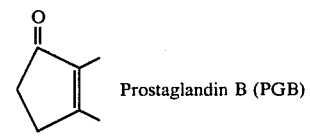 Prostaglandin A (PGA)

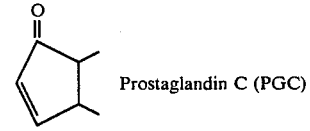 Prostaglandin B (PGB)

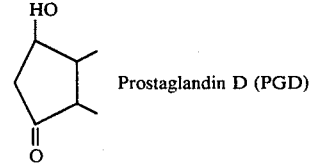 Prostaglandin C (PGC)

Prostaglandin D (PGD)

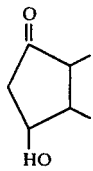

Prostaglandin E (PGE)

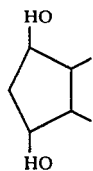

Prostaglandin F (PGF)

Endoperoxides

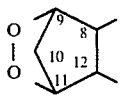

Prostaglandin G (PGG)
Prostaglandin H (PGH)

Thromboxanes

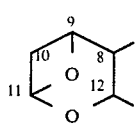

Thromboxane A (TXA)
(formula proposed by Hamberg and Samuelson "Thromboxanes: A New Group of Biologically Active Compounds Derived from Prostaglandin Endoperoxides", Proc. Natl. Acad. Sci. 70:899) (1973)

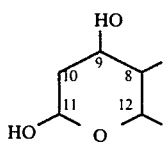

Thromboxane B (TXB)

The present invention is directed to novel substituted phenyl eicosanoid analogs having the formula:

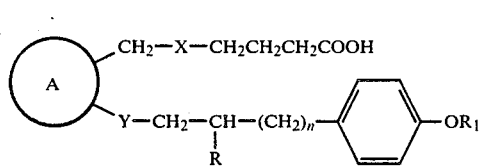
IV.

and their pharmaceutically acceptable esters and salts, wherein:

R is H or OH;
$R_1$ is H or lower alkyl;*
X is —$CH_2$—$CH_2$— or cis —CH=CH—;
Y is —$CH_2$—, $$-\underset{H}{\overset{|}{N}}-,$$

—O— or —S—;
n is 0 or 1; and

Ⓐ is (1) an eicosanoid nucleus (ring system) as previously defined, (2) a carbocyclic analog of an eicosanoid nucleus or (3) a heterocyclic analog of an eicosanoid nucleus wherein one of the carbons in a carbocyclic analog is replaced by O, S or N.

The preferred ring systems Ⓐ are:

*"lower alkyl" is used herein to refer to methyl, ethyl, propyl and butyl.

The present invention further provides pharmaceutical compositions containing one or more of these novel eicosanoid analogs and a method of inhibiting platelet aggregation in a mammal by administration of a therapeutically effective amount of such a compound or composition.

The present invention further provides radioactive derivatives of the compounds of formula IV which may be represented as:

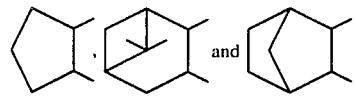
V.

wherein R, $R_1$, X, Y, n and Ⓐ are as previously defined, and Z is a radioactive atom. The preferred radioactive label Z is $I^{125}$ and, preferably, Z is at the 3' and/or 5' position. The pharmaceutically acceptable esters and salts of the labelled compounds of formula V are also considered to be included within the present invention.

In formulas IV and V above, the most preferred class of compounds are those having the carbocyclic analog of the thromboxane $A_2$ ring system, i.e., pinane analogs of the following formula:

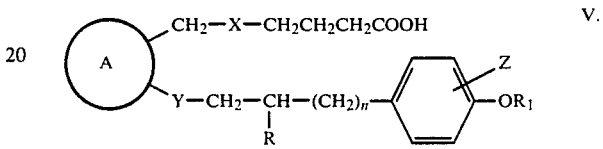
VI.

wherein R, $R_1$, Z and n are as previously defined; and m is 0, 1 or 2. Among the compounds of formula VI the most preferred are those wherein R is OH and $R_1$ is methyl (PTA-OM) and wherein R and $R_1$ are OH (PTA-OH).

Among the compounds of formulas IV and V tested to date, the compounds of formula VI above are the most potent antagonists of platelet aggregation and vasoconstrictors. Further, several of the compounds of formula VI tested to date are selective antagonists of either platelet aggregation or vasoconstrictors. For example, the present inventors have found that 13-aza-16-(p-hydroxyphenyl) pinane $TxA_2$ (PTA-OH) is more potent than 13-aza-16-(p-methoxyphenyl) pinane $TxA_2$ (PTA-OM) as an inhibitor of human platelet aggregation, whereas in tests on canine saphenous veins PTA-OM proved to be more potent than PTA-OH as an antagonist of vascular smooth muscle contraction. The selectiveness of these compounds is considered surprising in view of the fact that workers in this field had previously supposed that platelet aggregation and vascular smooth muscle contraction are mediated in the same manner.

The present invention further provides derivatives of 13-azaprostanoic acid of the following formula:

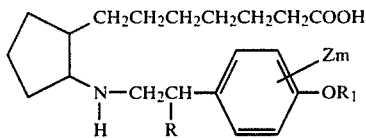

wherein R, $R_1$ and Z are as defined above, m is an integer of 0, 1 or 2 and their pharmaceutically acceptable esters and salts.

Among the compounds included in formula VII above, 7-(2-p-hydroxyphenethyl-amino-cyclopentyl)-heptanoic acid has two asymmetric centers and therefore exists as four stereoisomers. 7-(2-p-hydroxy-phenethanolamino-cyclopentyl)-heptanoic acid has three asymmetric centers and therefore exists as eight stereoisomers. Tests to date indicate that the activity resides primarily, but not exclusively, in the trans form compounds.

In formulas IV and V where Y is NH, O or S the compounds thus represented are antagonists of platelet aggregation and vasoconstrictors. In vitro tests have established that the compounds of formula VII above are thromboxane receptor blocking agents and that they inhibit arachidonic acid induced aggregation of human platelets. The compounds of formula VII have proven to be significantly more potent in inhibiting human platelet aggregation than 13-azaprostanoic acid (formula I) and the compounds of formula VI have proven to be yet more potent. Tests on canine saphenous veins have also shown that the compounds of formulas IV and V are potent antagonists of vasoconstrictors, i.e., antagonists of vascular smooth contraction. Antagonists of vasoconstrictors, e.g., the present compounds, differ from vasodilators in their mode of action. Tests using laboratory animals have further demonstrated that administration of a commpound of formula IV protects against endotoxic shock resulting from the subsequent administration of Salmonella endotoxin. These test findings indicate utility of the compounds of formula IV as drugs for thrombotic, vasospastic and bronchaspastic disorders, e.g., asthma and adult respiratory distress syndrome. The compounds of formula IV offer the potential for a new approach to therapy of these disorders.

In formulas IV and V where Y is methylene the compounds thus represented are agonists of platelet aggregation and vasoconstrictors, indicating utility in shock therapy, e.g., treatment of circulatory shock, endotoxic shock, septic shock and hypertensive disorders.

The discovered activity of the compounds of the present invention is surprising in light of a previous report that a phenyl substituted analog of azaprostanoic acid was inactive. Venton et al, *J. Med. Chem.*, supra.

All of the compounds of formulas IV, V, VI and VII tested to date, while active in their cis forms, are more active in the trans forms.

The radioactive compounds of formula V also exhibit significant platelet aggregation inhibiting activity but their primary application at the present time is in the study of thromboxane receptors. The activity of the iodinated compounds claimed here is considered surprising in view of the fact that iodination commonly changes the steric nature of a receptor-binding compound sufficiently to destroy the biological activity of the compound.

Pharmaceutically acceptable esters are those esters which are cleaved in vivo to release the free acid or a salt thereof.

The compositions of the present invention contain a pharmaceutically effective amount (1 to 100 mg/kg of body weight doses for antiplatelet therapy or 1 to 50 $\mu m$ in vitro) of one or more of the compounds of formulas IV and V above and/or their salts and esters in combination with pharmaceutically acceptable diluents, carriers, and/or excipients. The compounds are readily soluble in basic media such as aqueous sodium hydroxide and may be subsequently diluted in physiologic buffers. A dose of 30 mg/kg of trans APT was effective in protecting rats against the pathophysiologic sequelae of S. enteritidis endotoxemia.

Additional aspects and advantages of the present invention will become apparent from a reading of the following detailed description of the preferred embodiments.

DESCRIPTION OF THE PREFERRED EMBODIMENTS

I. Synthesis of 13-Azaprostanoic Acid Analogs

A.
7-(2-p-hydroxyphenethylamino-cyclopenthyl)-heptanoic acid (Compound A) and its ethyl ester

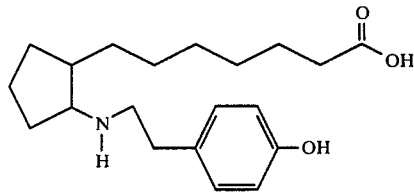

(A) 13-APT

Compound A was prepared in a manner analogous to 13 APA itself, i.e., by borohydride reduction of the Schiff base obtained from the reaction of tyramine and ethyl-2-oxo-cyclopentane-heptanoate. This reaction produces about equal amounts of the cis and trans ethyl esters, which were separated on preparative silica gel TLC and subsequently hydrolyzed to the free acids by refluxing in aqueous NaOH. Tests using both U46619 (9α,11α-methanoepoxy prostaglandin $H_2$) and arachidonic acid-induced platelet aggregation techniques showed that the two isomers were active, with the trans more potent than the cis. These results parallel the effects of 13-APA itself, which is also much more potent as the trans form, however, the Compound A is significantly more potent than the parent 13-APA.

(i) Preparation of
Benzyl-2-oxo-cyclopentanecarboxylate

A mixture of 50 g. of methyl-2-oxocylopentanecarboxylate and 50 g. of redistilled benzyl alcohol was heated at 160° C. under a stream of nitrogen in a 500 ml. flask for 20 hours. Methanol distilled off as it was formed. The reaction mixture was subsequently cooled and the mixture distilled on the kugelrohr apparatus. The benzyl alcohol was removed by heating to 120° C. at 2 mm and the benzyl ester collected at 130° C. Yield was 45 g. (59%).

(ii) Preparation of Ethyl-7-(1'-benzyloxycarbonyl-5'-oxocyclopentyl)-heptanoate

To a 100 ml. RB flask was added 13 g. to Ethyl-7-bromoheptanoate and 12.8 g. of 2-benzyloxycarbonyl-cyclopentanone. The reactants were dissolved in 50 ml. of anhydrous acetone and refluxed over 17 g. of anhydrous potassium carbonate under nitrogen for 20 hours. The reaction mixture was then cooled and filtered and the filtrate evaporated to afford 22.1 g. of crude oil, which was not further purified at this stage.

(iii) Preparation of Ethyl-7-(2-oxocyclopentyl)-heptanoate

The crude oil from (ii) above was dissolved in 50 ml. of toluene and reduced over 1 g. of 5% Pd on carbon under 50 psi of hydrogen for 20 hours. The catalyst was removed by filtration and the filtrate refluxed two hours to complete decarboxylation. The toluene was subsequently removed by evaporation and the residual oil distilled on the Kugelrohr apparatus. Heating to 130° C. removed the volatile impurities, and the bulk of the desired product was collected at 175°–180° C. Yield was 11.2 g. (79%).

(iv) Preparation of Ethyl-7-[2-(p-hydroxyphenethylamino)-cyclopentyl]-heptanoate (The ethyl ester of Compound A)

To a solution of 2.0 g. of Ethyl-7-(2-oxocyclopentyl)-heptanoate and 1.3 g. of tyramine free base in 50 ml. of anhydrous methanol contained in a 100 ml. flask was added 6 g. of 3A molecular sieves. This mixture was stirred at room temperature for 63 hours under nitrogen. The reaction mixture was then cooled in an ice bath and treated with 400 mg. of sodium borohydride. The mixture was stirred for 45 minutes at 0° C. and then 60 min. more at room temperature. The excess borohydride was destroyed by addition of 5 ml. of acetone. The mixture was filtered and the filtrate evaporated to an amber oil which was taken up in 100 ml. of ethyl acetate and extracted with 100 ml. of distilled water containing 4 ml. of acetic acid. The organic layer was separated and washed twice with distilled water and subsequently dried over magnesium sulfate and evaporated to an oily residue.

A portion of the mixture was resolved by preparative TLC (thin layer chromatography) on silica gel plates (2 mm thickness) using chloroform-ether (1-2). Each plate was developed three times to obtain the best resolution. The cis isomer moved faster and was pure after three developments on a single plate. The trans isomer was scraped off and redeveloped on additional plates two more times, each plate again being developed three times before scraping. By this method one can obtain about 40 mg. of trans ester and 140 mg. of cis ester, using a total of twelve plates (20×20 cm).

(v) Preparation of 7-(2-p-hydroxphenethylamino-cyclopentyl)-heptanoic acid (Compound A)

The isomers were each refluxed in 2.5 % NaOH (20 ml.) for four hours. The solutions were then cooled and acidified with glacial acetic acid and permitted to stand overnight to induce crystallization. The precipitates were filtered and washed with water, methanol and acetone and dried in vacuo. Yield of trans isomer was 21 mg., and yield of cis isomer was 75 mg. (58%).

Reaction Summary

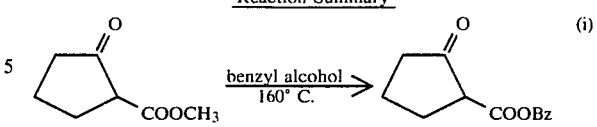

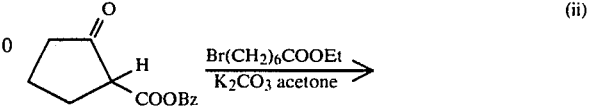

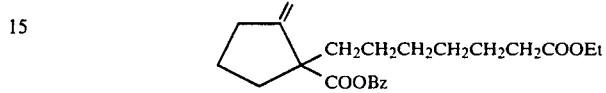

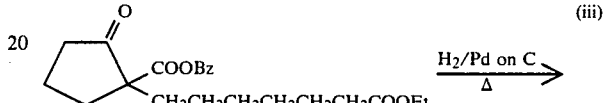

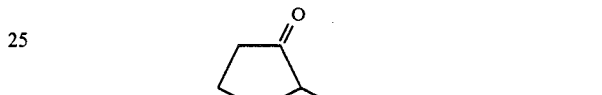

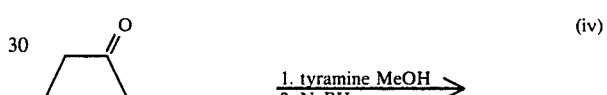

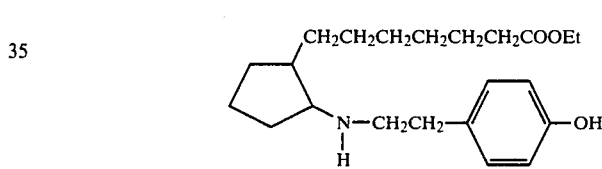

B. 7-(2-p-hydroxyphenylethanolamino-cyclopentyl)-heptanoic acid (Compound B) and its methyl ester

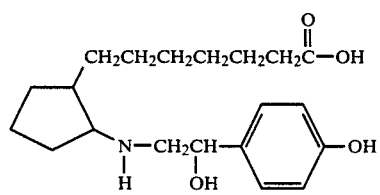

(B) 13-APO

The key intermediate in the synthesis of the 13-Azaprostanoic acid derivatives of the present invention is ethyl-(2-oxocyclopentyl)-heptanoate. In preparing this key intermediate in the synthesis of Compound A above, a sample of methyl-2-oxocyclopentylcarboxylate is transesterified with benzyl alcohol to the benzyl ester, which is subsequently coupled with ethyl-7-bromoheptanoate in acetone in the presence of potassium carbonate and reductively decarboxylated to the desired keto-ester intermediate. That route led to serious problems with side-products and low yields.

The synthesis described here utilizes a simpler route to the key intermediate, ethyl-(2-oxocyclopentyl)-heptanoate. This more preferred route was adapted by the present inventors from Novak and Szantay (SYNTHESIS, 353, 1974) and provided a much cleaner batch of intermediate and greatly improved yields of the intermediate. This preferred synthesis, described in detail below, treats methyl-2-oxocyclopentylcarboxylate with ethyl-7-bromoheptanoate directly and involves acid-catalyzed hydrolysis and decarboxylation of the resulting product to afford 7-(2-oxocyclopentyl)-heptanoic acid which was then re-esterified by treatment with excess ethereal diazomethane.

(i) Preparation of
Ethyl-7-(1'-methoxycarbonyl-5-oxocyclopentyl)-heptanoate

A mixture of 10 g. of ethyl-7-bromoheptanoate and 5.9 g. of methyl-2-oxocyclopentylcarboxylate was refluxed for 20 hours in 100 ml. of dry acetone over 13 g. of anhydrous potassium carbonate in a nitrogen atmosphere. After cooling, the reaction mixture was filtered and the solvent removed at the rotovap. The residual oil was distilled on the Kugelrohr apparatus, with some unreacted bromoheptanoate first collected at 80° C., followed by distillation of product at 140° C. A total of 10.9 g. of product was obtained, with about 12–15% O-alkylated material.

(ii) Preparation of 7(2-oxocyclopentyl)-heptanoic acid

A suspension of 10.9 g. of ethyl-7-(1'-methoxycarbonyl-5'-oxocyclopentyl)-heptanoate in 100 ml. of distilled water containing 6 g. of conc. sulfuric acid was refluxed under nitrogen. Progress of the reaction was followed by gas chromatography/mass spectroscopy analysis of a sample at intervals. After 48 hours the reaction was virtually complete and the mixture was cooled and extracted with one volume of ethyl ether. The aqueous layer was separated and extracted and extracted again with one volume of ether and the combined ethereal extracts were dried over magnesium sulfate and evaporated to a colorless oil which was sufficiently pure for the next step in the process. Yield was 6.6 g., about 99%.

(iii) Preparation of
Methyl-7-(2-oxocyclopentyl)-heptanoate

A 2.14 g. portion of 7-(2-oxocyclopentyl)-heptanoic acid was dissolved in 20 ml. of anhydrous ether and cooled to 0° C. in an ice bath. The stirred solution was then treated with ethereal diazomethane in about 1 ml. portions to control gas evolution until the yellow color persisted and bubbling was slow. The excess reagent was then blown off with a stream of nitrogen and the solvent evaporated at the rotovap. The residual oily ester was dried in vacuo over phosphorous pentoxide.

(iv) Preparation of
Methyl-7-[2-(p-hydroxyphenyl-ethanolamino)-cyclopentyl]-heptanoate (Methyl Ester of Compound B)

A solution of 4.35 g. of methyl-7-(2-oxocyclopentyl)-heptanoate and 2.95 g. of octopamine free base in 50 ml. of anhydrous methanol was treated with 10 g. of 3A molecular sieves and stirred under nitrogen for 96 hours. The reaction was cooled in ice and treated with 800 mg. of sodium borohydride in several portions to control foaming. The mixture was then stirred for 60 minutes in the cold and an additional 30 minutes at room temperature. The sieves were filtered off and the filtrate evaporated to an amber oil which was partitioned between 150 ml. of chloroform and 75 mil. of distilled water containing 1 ml. of glacial acetic acid. The organic layer was separated and dried over magnesium sulfate and evaporated to afford 6.7 g. of oily product mixture which was dried in vacuo.

The cis and trans isomers were separated by HPLC (High Performance Liquid Chromotography) on a Partisil M9 10/50 PAC column (a cyanopropyl-modified silica), eluted with chloroformmethanol (97-3) at 5 ml./min. while monitoring 254 nm. About 70 mg. could be injected at once without overloading, and the cis isomer eluted in about 15 minutes with the trans appearing at about 25 minutes. Run time was shortened by increasing flow rate to 9.9 ml./min. to collect the trans. Yield of the cis isomer was 2.18 g. and yield of trans was 2.4 g. Altogether this amounts to about 65% of theoretical. This technique provided virtually complete resolution of both cis and trans at about 70 mg. per injection and is much preferred to the use of TLC on silica gel as described above in connection with the synthesis of Compound A. In the case of the octopamine analog, this resolution technique also gave partial resolution of the diastereomers of the cis form.

(v) Preparation of trans-13-APO (Compound B)

A 500 mg. portion of trans-13-APO methyl ester was dissolved in 30 m. of 2.5% NaOH and refluxed under nitrogen for 4 hours. The reaction mixture was cooled and transferred to a 50 ml. plastic centrifuge tube and treated with one mol. of glacial acetic acid. The precipitate that formed was centrifuged at once and the supernatant decanted off and concentrated on the rotovap to about 15. ml. volume at which point a white solid was observed to precipitate. The solid was filtered off and washed with distilled water and ethanol and dried in vacuo. Yield of pure trans-13-APO was 290 mg. (60%).

A second hydrolysis using 600 mg. of ester which was refluxed in the base only 2 hours gave a product which contained several impurities. The crude solid was suspended in 10 ml. of ethanol (absolute) and refluxed briefly to dissolve the contaminants, then centrifuged and the supernatant decanted off. The solid was washed twice with 10 ml. of fresh ethanol and dried in vacuo. Yield was 350 mg. (62%).

(vi) Preparation of cis-13-APO (Compound B)

A 700 mg. portion of cis-13-APO methyl ester was dissolved in 30 ml. of distilled water containing 200 mg. of NaOH and the solution refluxed four hours and then cooled in ice. Addition of 400 microliters of glacial acetic acid gave an immediate precipitate which was centrifuged. The supernatant was concentrated at the rotovap to about 10 ml. volume, and the solid which separated was filtered off and washed with distilled water and dried in vacuo. TLC analysis showed several impurities persisted, and that considerable product was still in the filtrate. The dried solid portion was suspended in 8 ml. of ethanol and heated to boiling, sonicated briefly and allowed to cool. The insoluble solid was centrifuged and washed twice with 8 ml. portions of fresh ethanol, then recentrifuged and dried in vacuo. Yield of pure cis-13-APO was only 208 mg. (30%).

Another problem in the synthesis of Compound A as previously described was the appearance of contaminants in the product after alkaline hydrolysis of the methyl esters to the free acids. This is thought to be a result of limited degradation during the course of the heating, since similar impurties appear in both the 13-APO and 13-APT preparations for both cis and trans isomers. While attempting to recrystallize a batch of contaminated trans-13-APO from ethanol, it was discovered that the impurities were soluble in ethanol but the product was practically insoluble. consequently, washing with hot ethanol is effective in producing pure product following hydrolysis. Reducing the reflux time for hydrolysis from 4 hours to 2 hours gave improved yield, and this shorter reaction time seems advisable to minimize breakdown.

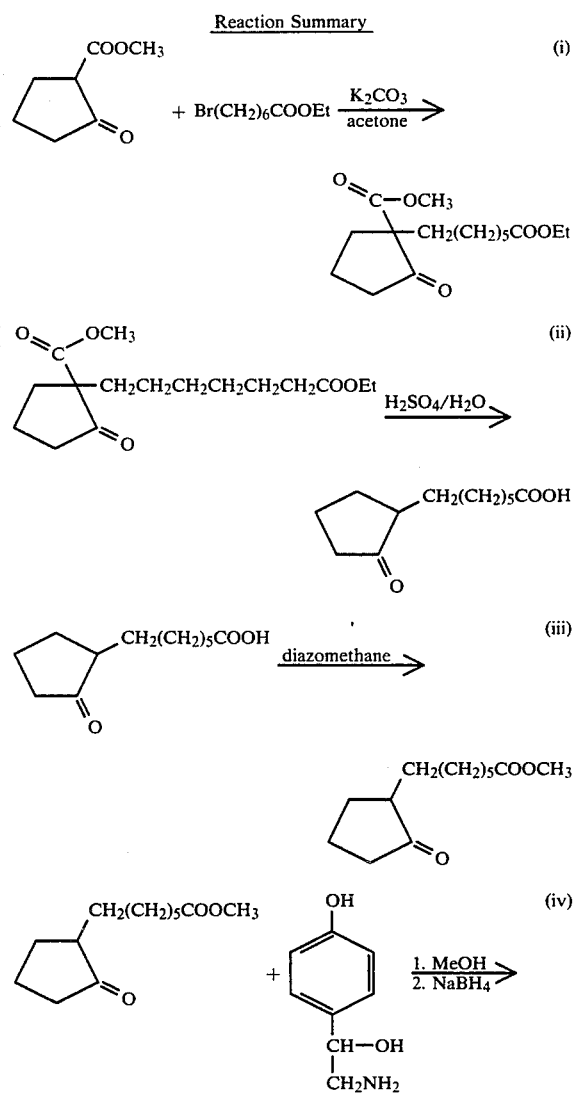

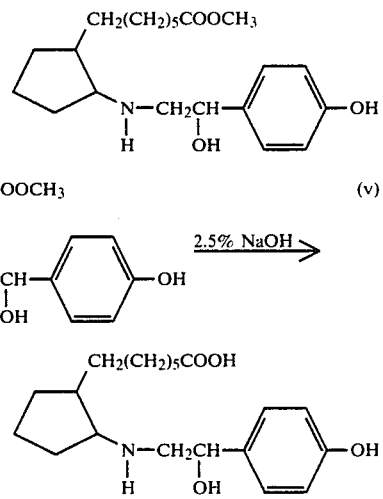

II. Biological Activity of 13-Substituted Derivatives of 13-Azaprostanoic Acid

A. Inhibition of human platelet aggregation

Platelet rich plasma was prepared from four healthy, normal volunteers using standard techniques. Platelet aggregation was measured in a platelet aggregometer using the technique of Born (G.V.R. Born, Nature 194, 927–929 (1962). Platelets were preincubated with indomethacin (10 $\mu$M) to inhibit endogenous arachidonic acid metabolism. The cis or trans isomers of 13-APT (A) and 13-APO and cis-iodo APO (B) were preincubated with platelets for one minute prior to aggregation with U46619, a thomboxane/prostaglandin endoperoxide mimetic. Inhibition of U46619 induced platelet aggregation by the move compounds was measured one minute after the start of the aggregation response. The approximate $ID_{50}$ values for the compounds are given below (Tables 1 and 2).

TABLE I $ID_{50}$ Values for 13-Substituted Derivatives of 13-Azaprostanoic Acid

| Compound | $ID_{50}$ |
|---|---|
| 13-cis-azaprostanoic acid | 14.8 ± 2.2 $\mu$M n = 5 |
| 13-trans-azaprostanoic acid | 13.6 ± 1.9 $\mu$M n = 5 |
| 13-cis-APT | 17.6 ± 4.4 $\mu$M n = 6 |
| 13-trans-APT | 9.9 ± 1.7* $\mu$M n = 6 |
| 13-cis-APO | 16.0 ± 3.2 $\mu$M n = 4 |
| 13-trans-APO | 8.3 ± 1.4+ $\mu$M n = 4 |

Platelets were aggregated with U46619 (0.5 to 1.0 $\mu$M) to produce an average % aggregation at one minute of 61.3 ± 3.1. The $ID_{50}$ values were calculated based on the inhibition of U46619 induced aggregation one minute after its addition.
*p < 0.02 compared to 13-cis-APT.
+p = 0.05 compared to 13-cis-APO.

TABLE 2

Comparison of the $ID_{50}$ Values of cis-APO and iodo-cis-APO

| Compound | $ID_{50}$ |
|---|---|
| 13-cis-iodo APO | 9.8 ± 1.3 $\mu$M n = 5 |
| 13-cis-APO | 6.4 ± 0.7 $\mu$M n = 5 |

Platelets were aggregated with U46619 (0.09 to 0.65 $\mu$M) to produce an average % aggregation at one minute of 47 ± 3. The $ID_{50}$ values were calculated based on the inhibition of U46619 induced aggregation one minute after its addition.

The above data is evidence that these compounds inhibit human platelet aggregation induced by a thromboxane/endoperoxide-mimetic.

B. Preparation of $^{125}$I radiolabelled compounds A and B

Both compounds were successfully iodinated using either the chloramine-T or lactoperoxidase method. Hunter, W. M. and F. C. Greenwood: "Preparation of Iodine-131 Labelled Human Growth, Hormone of High Specific Activity", *Nature,* 194, 495 (1962). These radiolabelled compounds were used to characterize human platelet thromboxane/PGH$_2$ and rat aortic receptors. Membranes from human platelets or rat aortas were prepared using standard techniques. Shepherd, G. L., P. J. Lewis, I. A. Blair, C. De Mey and J. MacDermot: "Epoprostenol (Prostacyclin, PGI$_2$) Binding and Activation of Adenylate Cyclase in Platelets of Diabetic and Control Subjects", *Br. J. Clin. Pharmac.,* 15: 77–81, 1983. In preliminary studies the estimated K$_d$ for compound B was 1,400 nM in human platelet membranes and 50 nM in rat aortic membranes.

This study provides evidence that these compounds may interact with specific platelet and vascular thromboxane receptors. This study also provides evidence that eicosanoid analogs may be iodinated ($^{127}$I or $^{125}$I) and still possess biological activity. Furthermore, this provides evidence for the concept that the synthetic approach to insert a phenol group into the molecule for the purpose of iodination outlined in this application may be applied to the study of eicosanoid receptors of other classes.

C. Activity against endotoxic shock

When pretreated with trans-13 APT, at a dose of 30 mg/kg, injected intraperitoneally, and administered Salmonella endotoxin intravenously, young male Long-Evans rats are protected against endotoxic shock. Plasma thromboxane B$_2$ levels, as measured 30 minutes and four hours after endotoxin administration are elevated to the same degree in both the trans-13 APT pretreated and vehicle treated animals; however, 6-keto-PGF$_{1\alpha}$ levels are significantly lower in the trans-13 APT pretreated rats as compared to the vehicle pretreated animals. The trans-13 APT pretreated animals are also less subject to endotoxic shock as measured by hypoglycemia, thrombocytopenia and tissue infarct effects, which are all observed in the vehicle pretreated animals. Based on the protective biological response observed and the absence of change in plasma thromboxane levels, it is concluded that trans-13 APT is a thromboxane receptor antagonist.

III. Synthesis of Pinane Analogs

A. Trans-2-(methyl-2(z)-heptenoate)-3-amino-6,6-dimethylbicylco[3.1.1] heptane (9)

Commercially available Nopol may be converted to its benzyl ether with benzyl chloride in DMF followed by hydroboration to give alcohol 2 (Fried et al., *Adv. Prostaglandins and Thromboxane Res.,* Vol. 6, pp. 427–436). The alcohol 2 may then be oxidized to ketone 3 with MnO$_2$ (Arnold et al., JACS 96, 4207) and the ketone protected as the ketal 4. Catalytic hydrogenation of 4 gives alcohol 5 which may be oxidized with pyridinium chlorochromate to yield aldehyde 6. Coupling of 6 with the appropriate Wittig reagent followed by estification gives compound 7 (Fried et al., *Adv. Prostaglandin and Thromboxane Res.,* vol. 6, pp. 427–436). Hydrolysis of ketal 7 gives the ketone 8 which may be reductively aminated to give intermediate amine 9 (Borch and Durst, JACS, 91, 3996).

B. Para-2,3-epoxyproplphenyl methoxymethyl ether 10

Epoxidation of p-allylphenyl methoxymethyl ether with m-chloroperbenzoic acid in methylene chloride gave 10 in 75% yield (b.p. 85°–92° at 0.5 mm). Para-allylphenyl methoxymethyl ether was prepared according to literature (Kitamura et al., *Tetrahedron,* 34, 3451 (1978).

C. PTA-OH

Into 5 ml of anhydrous MeOH was added 140 mg (0.5 mmole) of 9 and 108 mg (0.55 mmole) of 10. This solution was refluxed for 20 hours over nitrogen followed by the addition of 1.5 ml of 2.0 N NaOH and 4 more hours of refluxing. The mixture was brought to dryness under vacuum and 3ml of 0.5 N HCL added together with 3 ml acetic acid. This mixture was warmed to 90° for 1 min followed by evaporation of the solvents under vacuum. The remaining light yellow gum was taken up in chloroform-methanol (9:1) and chromatographed on silica gel using chloroform-methanol (9:1) as the mobile phase. This yielded pure PTA-OH (mixture of C-15 and epimers) as a white solid (mp 126°–128°). Yield 42%.

D. PTA-OM

Into 1 ml of anhydrous methanol was added 15 mg of PTA-OH and an excess of a diazomethane-ether solution. The yellow solution was stirred at room temperature for 30 min followed by evaporation of the solvent under a dry nitrogen stream. The gummy residue was dissolved in 2 ml methanol and 0.5 ml of 2 N NaOH followed by 4 hours of refluxing. At the end of the reflux period, 1 ml of acetic acid was added to neutralize the NaOH and the solvents were evaporated under vacuum. The residue was taken up in chloroform-methanol (9:1) and chromatographed as described for PTA-OH. This yielded pure PTA-OM as a glassy solid. Yield 68%.

E. ω-Contracted Analog, 11

Into 3 ml of anhydrous methanol was added 70 mg (0.25 mmole) of 9 and 33 mg (0.3 mmole) of styrene oxide. This solution was refluxed for 20 hours over nitrogen followed by the addition of 0.75 ml of 2 N NaOH for 4 more hours of refluxing. The solution was cooled to room temperature and 2 ml of acetic acid added and the entire mixture evaporated to dryness under vacuum. The resulting gummy material was taken up in chloroform-methanol (9:1) and chromatographed as described for PTA-OH. This yielded the ω-contracted compound 11 as a glassy solid. Yield 61%.

REACTION SUMMARY

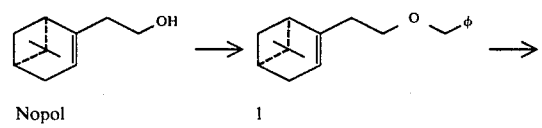

-continued
REACTION SUMMARY

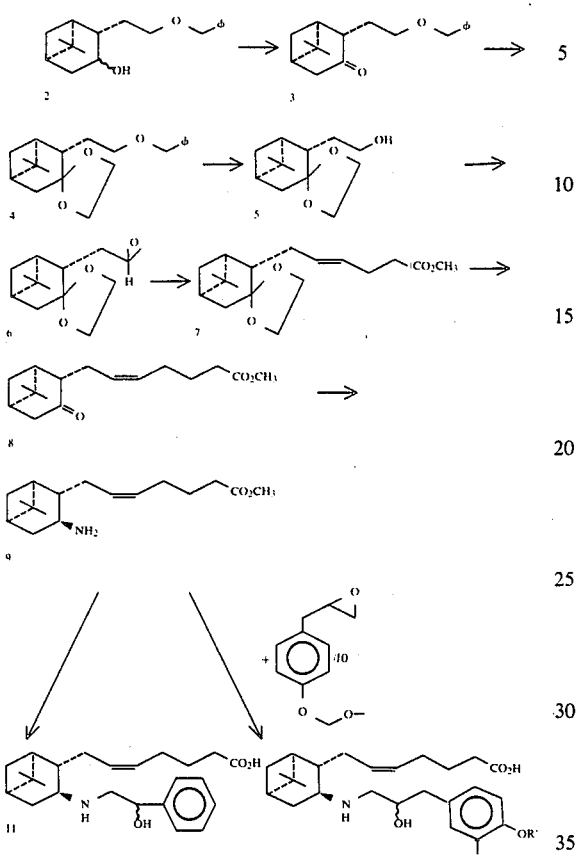

PTA—OH: R = R' = H
PTA—OM: R' = Me, R' = H
Iodo-PTA—OH: R = I, R' = H

IV. Biological Activity of the Pinane Analogs

The potency of PTA-OH and PTA-OM for antagonism of U46619 induced human platelet aggregation was determined as described above. The $ID_{50}$ for each compound is given below.

PTA-OH (n=11): 0.52±0.07 μM
$^{127}$I-PTA-OH (n=4): 0.38±0.05 μM
PTA-OM (n=11): 1.56±0.35 μM

Thus, iodination of PTA -OH did not result in any significant loss of biological activity.

V. Synthesis of Carbocyclic Analogs of Endoperoxides

A convenient starting point for the synthesis of the carbocyclic endoperoide analogs is Norcamphor which is a commerically available compound having the formula:

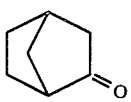

The norcamphor may be alkylated, in a conventional alkylation technique, with methyl 7-bromo-5-cis-heptenoate (described in U.S. Pat. No. 3,773,795) in the presence of lithium diisopropylamide to yield

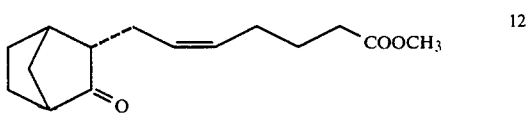

which when incorporated, in place of compound 8, in the synthesis described for the pinane analogs will yield compounds of the formula:

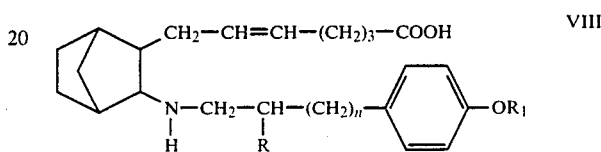

wherein R, $R_1$ and n are as previously defined. The compounds of formula VIII may be labelled with a radioactive atom as previously described.

The invention may be embodied in other specific forms without departing from the spirit or essential characteristics thereof The present embodiments are, therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:
1. Radioactive compounds of the formula:

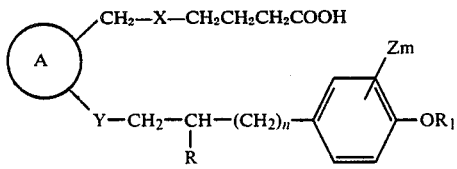

and their pharmaceutically acceptable esters and salts, wherein:
R is H or OH;
$R_1$ is H or lower alkyl;
X is —$CH_2$—$CH_2$— or cis —CH=CH—;
Y is —$CH_2$—,

—O— or —S—;
n is 0 or 1;
m is 1 or 2;
Z is radioactive iodine; and
Ⓐ is
(i) an eicosanoid nucleus;

(ii) a carbocyclic analog of an eiconsanoid nucleus; or (iii) a heterocyclic analog of an eicosanoid nucleus wherein one of the carbons in one of said carbocycliic analogs is replaced by O, S or N.

2. The compounds of claim 1 wherein Ⓐ is a divalent nucleus selected from the group consisting of:

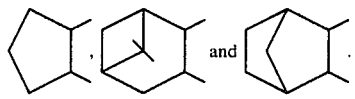

3. A radioactive compound is accordance with claim 1 wherein Z is $I^{125}$.

4. A radioactive compound in accordance with claim 3 wherein Z occupies the 3' and/or 5' position.

5. The trans isomers of the compounds of claim 1.

6. Radioactive compounds of the formula:

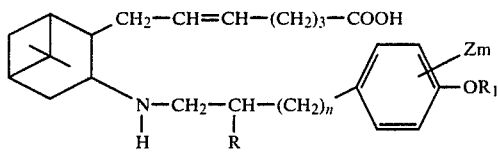

and their pharmaceutically acceptable esters and salts, wherein:
R is H or OH;
$R_1$ is H or lower alkyl;
n is 0 or 1;
Z is radioactive iodine; and
m is 1 or 2.

7. The compound of claim 1 wherein Z is $I^{125}$ and is at the 3' and/or 5' position.

8. The trans form compounds of claim 7 wherein R is OH and $R_1$ is methyl.

9. Radioactive 13-azaprostanoic acid derivatives of the forumla:

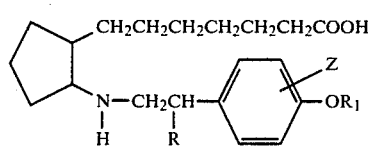

wherein R is H or OH, $R_1$ is H or lower alkyl and Z is a radioactive iodine, and their pharmaceutically acceptable esters and salts.

10. A radioactive compound in accordance with claim 9 wherein Z is $I_{125}$.

11. A radioactive compound is accordance with claim 10 wherein Z occupies the 3' and/or 5' position.

* * * * *

UNITED STATES PATENT AND TRADEMARK OFFICE
CERTIFICATE OF CORRECTION

PATENT NO. : 4,695,647

DATED : September 22, 1987

INVENTOR(S) : Eller et al

It is certified that error appears in the above—identified patent and that said Letters Patent is hereby corrected as shown below:

OTHER PUBLICATIONS, line 10, "pp. 420-4210" should read --pp. 4207-4210--.

Col. 1, line 3, "29556" should read --29566--.

Col. 2, line 4. "casade" should read --cascade--;

lines 7-15, formula reads:

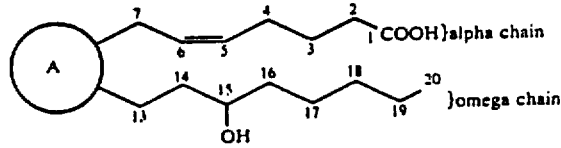

formula should read:

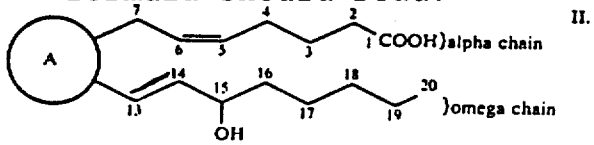

Col. 4, line 47, "and wherein R and $R_1$ are OH" should read --or H--.

Col. 5, line 38, "commpound" should read --compound--;

line 42, "bronchaspastic" should read --brochospastic--;

line 48, "agonists" should read --antagonists--.

UNITED STATES PATENT AND TRADEMARK OFFICE
CERTIFICATE OF CORRECTION

PATENT NO. : 4,695,647

DATED : September 22, 1987

INVENTOR(S) : Eller et al

It is certified that error appears in the above—identified patent and that said Letters Patent is hereby corrected as shown below:

Col. 6, line 6, "µm" should read --µM--.

Col. 12, line 40, "move" should read --above--.

Col. 15, line 56, "endoperoide" should read --endoperoxide--.

Col. 16, line 33, after "thereof" insert --.--.

Col. 18, line 26, "$I_{125}.$" should read --$I^{125}.$--.

Signed and Sealed this

Twenty-ninth Day of August, 1989

Attest:

DONALD J. QUIGG

Attesting Officer

Commissioner of Patents and Trademarks